(12) United States Patent
Wu et al.

(10) Patent No.: US 9,298,076 B2
(45) Date of Patent: Mar. 29, 2016

(54) IMAGE PROJECTOR

(71) Applicant: Hong Kong Applied Science and Technology Research Institute Co. Ltd., New Territories (HK)

(72) Inventors: Changli Wu, Shenzhen (CN); Xuyan Huang, Kowloon (HK); Ying Liu, New Territories (HK)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 228 days.

(21) Appl. No.: 14/147,577

(22) Filed: Jan. 5, 2014

(65) Prior Publication Data

US 2015/0193978 A1   Jul. 9, 2015

(51) Int. Cl.
*G03B 21/28*   (2006.01)
*G03B 21/14*   (2006.01)

(52) U.S. Cl.
CPC .............. *G03B 21/28* (2013.01); *G03B 21/142* (2013.01)

(58) Field of Classification Search
CPC .. G03B 21/28; G03B 21/204; G03B 21/2013; G03B 21/2033; G06T 19/006
USPC .................... 353/20, 28, 30, 31, 98
See application file for complete search history.

(56) References Cited

U.S. PATENT DOCUMENTS

| 5,969,754 A | 10/1999 | Zeman |
| 6,556,858 B1 | 4/2003 | Zeman |
| 8,244,333 B2 | 8/2012 | Wood et al. |
| 8,364,246 B2 | 1/2013 | Thierman |
| 8,434,873 B2 | 5/2013 | Feng et al. |
| 2007/0158569 A1 | 7/2007 | Zeman |
| 2010/0110385 A1* | 5/2010 | Choi ..................... G06F 1/1626 353/20 |
| 2010/0165297 A1* | 7/2010 | Mizushima ........ G02B 26/0875 353/30 |
| 2010/0328627 A1* | 12/2010 | Miyazaki ............. G02B 26/008 353/85 |
| 2012/0032875 A1* | 2/2012 | Sprowl ................... G02B 27/01 345/156 |
| 2012/0038693 A1* | 2/2012 | Kang ................... H04N 9/3117 345/691 |
| 2012/0140189 A1* | 6/2012 | Hiranuma .............. G03B 17/54 353/69 |
| 2013/0100417 A1* | 4/2013 | Yang .................... G03B 21/204 353/31 |

FOREIGN PATENT DOCUMENTS

| CN | 1758875 A | 4/2006 |
| CN | 101166467 A | 4/2008 |
| CN | 101686820 A | 3/2010 |
| CN | 101883522 A | 11/2010 |
| CN | 202821303 U | 3/2013 |
| CN | 103006180 A | 4/2013 |

* cited by examiner

*Primary Examiner* — Sultan Chowdhury
(74) *Attorney, Agent, or Firm* — Eagle IP Limited; Jacqueline C. Lui

(57) ABSTRACT

An image projector for augmenting the appearance of a physical object is disclosed, also known as an augmented reality projector. The augmented reality projector comprises an optical arrangement to provide the possibility of precise matching of a projected image of the physical object back onto the object itself, instead of using digital image processing to do so. Digital image processing may be used to enhance features of the image and is not required for resizing or orienting the image to the object. This reduces the need for computational power to process the image and spares processing resources to refresh the image in real time. Accordingly, the processed image can be refreshed to change the appearance of a moving object. Furthermore, the precise matching provides the possibility of using projected images a graphical use interface, as movements of a user's fingers on the interface can be determined accurately.

17 Claims, 18 Drawing Sheets

IMAGE PROJECTOR

FIELD OF INVENTION

This invention relates to image projectors and particularly to augmented reality projectors useful for augmenting the appearance of physical objects.

BACKGROUND OF INVENTION

An image projector such as an augmented reality projector changes the appearance of a physical object by projecting an image onto the object. Patterns, colours and visible textures are super-imposed onto the surface of the object to make the object look different or to provide information on the surface.

Augmented reality is useful for ensuring success in some medical procedures such as microsurgical or cosmetic procedures, even surgery on delicate human arts such as the human brain and so on. For example, a medical professional may find it difficult to appreciate the internal structure of a human part right underneath its skin just by looking at the surface of the part. The colour, glare and distribution of ambient light may smooth out and obscure superficial textures and reliefs. Thus, determining the exact locations of under-skin or subcutaneous parts such as major blood vessels can be difficult even in a well-lit environment and more so if the blood vessels lie under a significant deposit of subcutaneous fat. An augmented reality projector capable of differentiating subcutaneous structure may be used to mitigate this difficulty by enhancing visual contrast, for example, between subcutaneous blood vessels and surrounding tissues. The augmented reality projector for such medical applications may comprise an infrared imaging element. Blood protein in subcutaneous blood vessels absorbs near-infrared wavelengths while the surrounding tissues tend to reflect them. Thus, a negative infrared image can be captured with dark parts showing blood vessels in the human part and illuminated parts showing the surrounding tissues. The augmented reality projector then generates a positive image in visible colours based on the infrared image, which is projected onto the same human part to highlight the locations of blood vessels under the skin. For better indication of the blood vessels, the projected image may have been treated to increase image contrast, or to enhance edge detection and so on.

However, the usefulness of this technology is limited because currently available augmented reality projectors cannot achieve good field-of-view match between the projected image and the object; they are unable to provide faithful image size reproduction and cannot provide sufficient precision in coinciding the image onto the object due to angular mismatch between the infrared imaging element and the image projector. Digital signal processing techniques have been the option of choice to overcome this mismatch instead of the relatively tedious option of designing an optical system to do so. The infrared image is processed digitally to adjust the size and angle of the projected image to fit object. However, such digital signal processing techniques have been found inadequate for achieving highly precise field-of-view match, possibly because there are simply too many variables to calculate. Furthermore, such digital signal processing techniques requires high processing power and tends to compete for computing resources in a multi-tasking environment. Thus, an augmented reality projector is often unable to refresh the projected image smoothly and in real time. This limits the technology from being applied to augment the appearance of moving objects.

Moreover, augmented reality projectors tend to have an infrared light source to supply infrared for illuminating objects such as the human part. However, the luminance distribution of the projected image and that of the infrared are not the same, making the image look less integral on the object.

Therefore, it is desirable to provide an augmented reality projector which can give a good field-of-view match between the image and the object, and by which the image may be updated sufficiently quickly to follow the changes of a moving object.

SUMMARY OF INVENTION

In a first aspect, the present invention proposes an image projector comprising: an imaging-element for capturing an image of an object in a reception-path in at least one first wavelength, a projection-element for projecting an image onto the object in an projection-path in at least one second wavelength, a wavelength selective interference-splitter for reflecting either one of the at least one first wavelength and the at least one second wavelength, and allowing passage of the other one of the at least one first wavelength and the at least one second wavelength, the imaging-element and the projection-element arranged such that either one of the projection-path and the reception-path passes through the interference-splitter, while the other one of the projection-path and the reception-path is reflected by the interference-splitter, the interference-splitter coinciding the projection-path and the reception-path between the interference-splitter to the object, the interference-splitter separating the projection-path and the reception-path from the interference-splitter to the respective projection-element and imaging-element, wherein the projection-path between the projection-element to the interference-splitter is conjugate with the reception-path between the interference-splitter and the imaging-element.

'Conjugate' means, for optical purposes, that the projection-path between the projection-element to the interference-splitter has the same distance as the reception-path between the interference-splitter and the imaging-element, and that the angle of the projection path to the effective plane of the interference-splitter is the same as the angle of the reception-path to the effective plane of the interference-splitter.

'Coinciding' or 'coincident' has the usual geometric meaning, and includes meaning two or more lines lying one on the other exactly, or two or more points being in exactly matching in position. In this specification, as the skilled man will understand, 'coinciding' two paths means causing the two paths to travel in entirely the same path but their directions of travel may be opposite.

Advantageously, the separated part of the projecting path and the reception-path provides the possibility of isolating the imaging-element from the projection-element. This leads to reduction of interference between the two elements. However, despite their mutual isolation, the conjugated positions of both elements to the interference filter in combination with the coincident part of the projection-path and the reception-path provide the possibility of excellent field-of-view match.

Typically, the imaging-element has a sensor surface, the projection-element has a projection surface, and the area of the sensor surface and the area of the projection surface are substantially the same. Alternatively, the projection-element has a projection surface, imaging-element including a field aperture, the field aperture being the part of the imaging-element conjugate to the interference-splitter, and the field aperture is suitable for cropping an image received on the field aperture to have substantially the same area as the projection surface. Using a field aperture allows the freedom to use projection-elements and imaging-elements with non-matching areas.

Having the "same area" here is understood by the skilled reader to include size, that is, include having the same aspect ratio. This is so that the image formed on the imaging-element may have substantially the same aspect ratio as the image formed on the projection surface.

Typically, the image projected by the projection-element is the image of the object captured by the imaging-element. However, it is preferable that the image is an enhanced image. Alternatively, the image projected by the projection-element is not an image of the object but is a graphical user interface capable of interacting with the object. In this case, it is preferable that the image projected by the projection-element is an image which has a blacked-out portion, and the back-out portion having a matching field-of-view with the object. This prevents the graphical user interface from being cast onto the object interacting with the graphical user interface.

Typically, but not necessarily, the at least one first wavelength is invisible to the human eye such as infrared or ultraviolet and the at least one second wavelength is within the visible range of wavelengths.

Typically, a projection lens is placed between the interference-splitter and the object so that the image projected by the projection-element and the image captured by the imaging-element has the same illuminance distribution from the projection lens.

Optionally, the interference-splitter is encapsulated in a polyhedron prism, such as a hexahedron prism. The different surfaces of the polyhedron may be used to receive and emit light at right angle to the different surfaces to reduce refraction and aberration.

Optionally, the image projector further comprises: a second imaging-element, and the prism capsulate a second interference-splitter, wherein the second interference-splitter further separates the projection-path and a second reception-path to the respective projection-element and the second imaging-element, and the projection-path between the projection-element to the interference-splitter is conjugate with the second reception-path between the interference-splitter and the second imaging-element.

In a second aspect, the invention proposes a graphical user interface projected from a projector as described above.

In a third aspect, the invention proposes an interactive keyboard projected from a projector as described above.

In a fourth aspect, the invention proposes an image projector comprising: a first light-source for projecting light onto an object in an incident-path in at least one first wavelength; a projection-element for projecting an image onto the object in an projection-path in at least one second wavelength; a wavelength selective interference-splitter for reflecting either one of the at least one first wavelength and the at least one second wavelength, and allowing passage of the other one of the at least one first wavelength and the at least one second wavelength; the light-source and the projection-element arranged such that either one of the projection-path and the incident-path passes through the interference-splitter, while the other one of the projection-path and the incident-path is reflected by the interference-splitter; the interference-splitter coinciding the projection-path and the incident-path between the interference-splitter to the object; the interference-splitter separating the projection-path and the incident-path from the interference-splitter to the respective projection-element and light-source.

The advantage of this arrangement is that the light of the second wavelength travels in a separate path to that of the light of the first wavelength until they coincide at the interference filter. Typically, the second wavelength is used for projecting an image and has a strong intensity. However, the light of the first wavelength is usually used for illuminating an object and is less intense. By have separate paths until the point of coincidence, light in the first wavelength is not subject to any effect causing energy loss or dissipation to the second wavelength. This helps to maintain strong illumination on the object in the second wavelength without needing a very intense source.

Furthermore, where the first wavelength and second wavelength coincides from the interference-splitter to the object, light in the first wavelength and light in the second wavelength can be cast with identical angle and distribution of illuminance onto the object, which is preferably as even as possible. In this case, where an image of the object is captured in the first wavelength and the image is re-cast back onto the object in the second wavelength, the re-cast image can have the same distribution of shadow, light and contrast as the object.

BRIEF DESCRIPTION OF FIGURES

Non-limiting, exemplary embodiments of the invention will now be described with reference to the following drawings, in which like reference number refers to like parts, wherein.

DETAILED DESCRIPTION OF THE PREFERRED EMBODIMENTS

Figure 1:
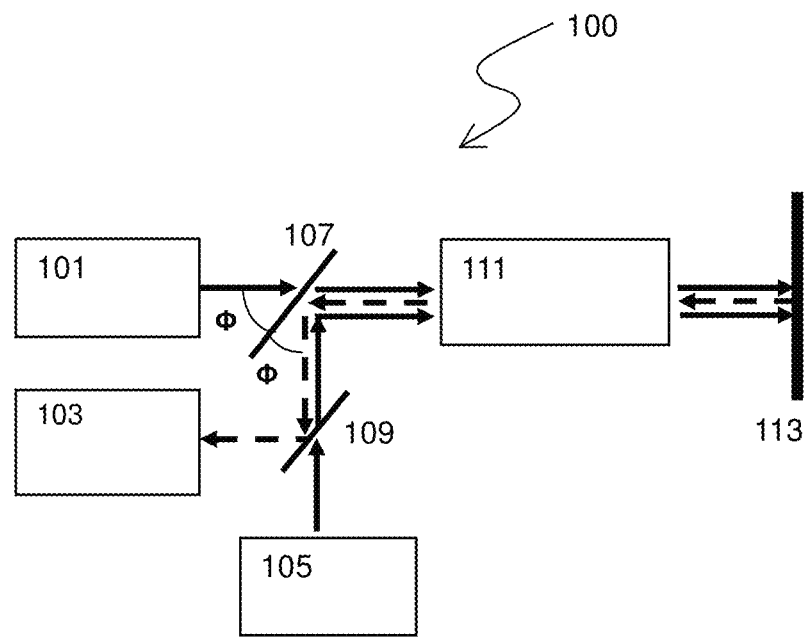
FIG. 1 is a schematic illustration of an embodiment of the invention.

FIG. 1 is a simple schematic of a general embodiment, which is an augmented reality projector 100.

The augmented reality projector 100 comprises a projector-element 101, a light-source 105, an imaging-element 103, a wavelength-selective interference-splitter 107, a half-mirror 109 and a projection-lens 111.

The projector-element 101 is capable of projecting images in a first wavelength. The light-source 105 is capable of emitting light in a second wavelength, different to that of the projector-element 101. Thus, there are two sources of electromagnetic radiation in the embodiment 100, namely the light-source 105 and that of the projector-element 101. The imaging-element 103 is capable of capturing images in the second wavelength.

In one direction, the projection-lens 111 focuses projections from the projector-element 101 onto an object 113, which may be an artefact, a wall or a projector screen. In the reverse direction, the projection-lens 111 focuses an image of the object 113 onto the imaging-element 103. Thus, the projector-element 101 and the imaging-element 103 are positioned in the focal plane of the projection-lens 111 but on the opposite side to the object 113. The object 113 in this case is an object which could be examined in the second wavelength for information not detectable in the first wavelength. The object 113 is not part of the embodiment and is illustrated only for the purpose of explaining the embodiment.

Light in the second wavelength is emitted from the light-source 105 and the light passes through the half-mirror 109, and is then reflected by the interference-splitter 107 to be focused by the projection-lens 111 onto the object 113. The object 113 reflects the light in the second wavelength which travels back through the projection-lens 111, is deflected by the interference-splitter 107, and then deflected by the half-mirror 109 to be focused on the imaging-element 103.

An image captured by the imaging-element 103 is transmitted to the projector-element 101. The projector-element 101 projects the image onto the object 113 through the projection-lens 111 in the first wavelength subsequently.

The optical path between the projector-element 101 to the object 113, and the optical path between the object 113 to the imaging element 103 are partially coincident and partially separate. The coincident part of these two paths lie between the interference-splitter 107 and the object 113, and the separate parts of these two paths respectively lie between the interference-splitter 107 and the projector-element 101, and then between the interference-splitter 107 and the imaging-element 103.

To provide a matching field-of-view, the projector-element 101 is conjugate with the imaging-element 103 to the interference-splitter 107. 'Conjugate' means that the distance between the interference-splitter 107 and the projector-element 101 is substantially the same as the distance between the interference-splitter 107 and the imaging-element 103, and that the angle $\phi$ at which the light in the second wavelength is reflected from the interference-splitter 107 is the same as the angle $\phi$ in which the light in the first wavelength from the projector-element 101 is incident on the interference-splitter 107 to pass through the interference-splitter 107. In FIG. 1, $\phi$ is illustrated to be forty-five degrees 45° to the plane of the interference-splitter 107.

Typically, the processed image is accentuated, enhanced or processed in any other way to make more prominent or subdued features of the object 113. The visual appearance of the object 113 is augmented by the projector-element 101 in this way. The processed image is said to have a matching 'field-of-view' if it overlays the object 113 in matching size, orientation and angle, and an observer will hardly notice that changes on the object 113 surface is due to a projected image.

It is possible that the light-source 105 is positioned to supply light onto the object 113 without the light transmitting through the projection-lens 111, such as from the side of the object 113, but it is preferably that the optical path between the projector-element 101 to the object 113 and the optical path between the light-source 105 to the object 113 are also coincident between the interference-splitter 107 and the object 113. This preferable arrangement provides a luminance distribution of the light in the second wavelength which is uniform with the luminance distribution in the projection from the projector-element 101. The field-of-view match will be even better in this case as the projected image, the captured image and the light emitted by the light-source 105 are all subject to the same luminance distribution, or transfer function, in the projection-lens 111.

Figure 2:
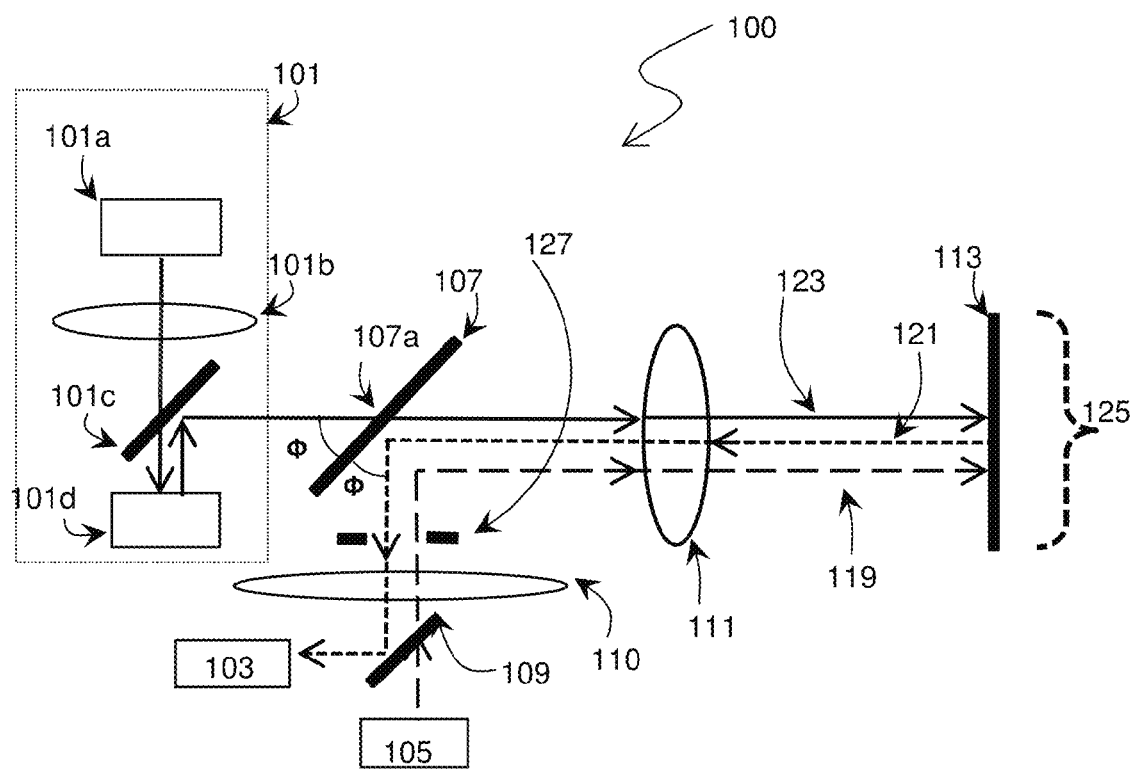
FIG. 2 is a schematic illustration of the embodiment of FIG. 1 in greater detail.

FIG. 2 is the schematic of FIG. 1 in greater detail. The first wavelength in this case is a monochromatic wavelength or a range of wavelengths visible to the human eye. The second wavelength in this case may be any monochromatic or a range of infrared wavelengths. The object 113 in this case would be an object which could be examined in infrared for information not detectable in visible light. For example, the object 113 may be a human hand and blood vessels inside the hand being the subject of study, in which case the infrared is near-infrared. Near-infrared is absorbed by blood protein but not by tissues surrounding blood vessels. Therefore, using near-infrared allows a negative infrared image to be captured where dark portions show blood vessels and bright portions show other parts of the hand.

The wavelength selective interference-splitter 107 in this case is a hot-mirror 107. A hot-mirror 107 is capable of reflecting 'warm' light in low wavelengths such as infrared but allowing 'cool' wavelengths such as visible light to pass through. Infrared emitted from the infrared-source 105 travels through the half-mirror 109, through a field aperture 127 and then through an illumination lens 201, and arrives at the hot-mirror 107 at an incident angle of $\phi$ to the effective plane of the hot-mirror 107, and is reflected by the hot-mirror 107 to be cast onto the object 113 through the projection-lens 111. The illumination lens 201 is used to provide illuminance distribution to ensure that the infrared is as evenly dispersed onto the object 113 as possible, which provides the possibility of sharp contrast between the different parts of the object 113 which respond differently to infrared. Uneven distribution could compromise sharpness of contrast and accuracy in the captured image. The hot-mirror 107 then deflects the infrared towards the object 113 at a point of deflection 107a.

The path of the infrared from the infrared-source 105 to the half-mirror 109, then from the half-mirror 109 to the illumination lens 110, then from the illumination lens 110 to the hot-mirror 107, and then through the projection-lens 111 to the object 113 shall be called the 'infrared incident path' 119 here.

When the infrared hits the object 113, the infrared is reflected and returns back towards the hot-mirror 107. The infrared is reflected by the hot-mirror 107 at a reflection angle $\phi$ to the effective plane of the hot-mirror 107, at the point of deflection 107a. Thus, the hot-mirror 107 deflects the returning infrared towards the field aperture 127, and then towards the half-mirror 109. The half-mirror 109 allows light of the same wavelength to pass through from one side of the half-mirror 109 to the other but deflects the light from passing through in the reverse direction. In this way, the infrared is diverted towards the infrared imaging-element 103 by the half-mirror 109 without reaching the infrared-source 105.

The returning infrared path from the object 113 back to the hot-mirror 107, from the hot-mirror 107 to the field aperture 127, from the field aperture 127 to the half-mirror 109, and from the half-mirror 109 to the infrared imaging-element 103 is termed the 'infrared-reception-path' 121.

The negative infrared image captured by the infrared imaging-element 103 is converted into a positive image in visible colours and is transmitted to the projector-element 101 and projected back onto the object 113 in visible light. The means for transmitting the image from the imaging-element 103 to the projector-element 101 can be any electrical means or microcontroller as would be known to the skilled man and which needs no elaboration here. As the infrared image is re-cast onto the object 113 in visible colours, features of the object 113 which were not visible to the human eye before such as blood vessels under the skin of the hand are now indicated on the surface of the object 113.

The projector-element 101 is preferably an LCOS system. 'LCOS' stands for Liquid Crystal Over Silicon, which is a technology for projecting images by reflecting visible light. The LCOS system comprises an LCOS panel 101d which is a layer of many liquid crystals secured on a silicon backplane. Polarity of an incident light ray hitting on a liquid crystal may be changed on being reflected by the liquid crystal. The shape of each liquid crystal in the LCOS panel 101d can be controlled electrically to determine if the liquid crystal should reflect and change the polarity of an incident ray of light. Generally, each crystal corresponds to a pixel in an image to be projected on the object 113 by the reflected light. Therefore, the LCOS system also comprises a visible light source 101a to illuminate the LCOS panel 101d.

Light from the visible light source 101a passes through an illumination lens 101b and then through a polarised beams splitter 101c so that only visible light of one polarity reaches the LCOS panel 101d. The LCOS panel 101d then reflects the visible light back towards the polarised beams splitter 101c. A portion of the reflected light has its polarity changed by the LCOS panel 101d such that this portion cannot pass through the polarised beams splitter 101c but is deflected by the orientation of the polarised beams splitter 101c towards the hot-mirror 107. The remaining portion of the reflected light which has not been changed in polarity passes back through the polarised-beam-splitter 101c into oblivion.

LCOS panel 101d is in effect a surface area on which the image to be projected is formed. Thus, the portion of the visible light deflected towards the hot-mirror 107 carries an image constructed by the liquid crystals in the LCOS panel 101d. The visible light passes through the hot-mirror 107 as the hot-mirror 107 only reflects low wavelength light such as infrared and is focused by the projection-lens 111 onto the object 113.

The polarised-beam-splitter 101c is positioned such that the visible light is projected onto the object 113 in a 'projection-path' 123. The projection-path 123 is incident on the effective plane of the hot-mirror 107 at an angle φ, and is coincident with the incident-infrared-path 119 and the infrared-reception-path 121 between the hot-mirror 107 and the object 113 at the 'point of deflection' 107a on the hot-mirror 107. Accordingly, it will be more appropriate from here onwards in the description to describe the 'point of deflection' 107a as the 'point of coincidence' 107a.

For clarity, FIGS. 1 and 2 illustrate the incident-infrared-path 119, the infrared-reception-path 121 and the projection-path 123 as separate lines between the hot-mirror 107 and the object 113. The skilled reader will understand that the incident-infrared-path 119, the infrared-reception-path 121 and the projection-path 123, are all coincident between the point of coincidence 107a and the object 113 and lie exactly on one another. However, the parts of the projection-path 123 and the infrared-reception-path 121 which are not between the point of coincidence 107a and the object 113 are separate. In other words, the part of the projection-path 123 between the LCOS panel 101d to the point of coincidence 107a and the part of the infrared-reception-path 121 between the point of coincidence 107a to the infrared imaging-element 103 are not coincident but are separate.

'Coinciding' or 'coincident' has the usual geometry meaning, which includes meaning two or more lines lying one on the other exactly, or meaning two or more points being exactly matching in position. Furthermore, 'coinciding' two paths means causing two paths to travel entirely between the same two points but their directions of travel may be opposite in this specification, such as the projection-path 123 and the infrared-reception-path 121.

The incident-infrared-path 119, the infrared-reception-path 121 and the projection-path 123 are either incident or reflective to the effective plane of the hot mirror at the same angle φ, such that the angle between the infrared-reception-path 121 and the projection-path 123 is 2×φ. In other words, the effective plane of the hot-mirror 107 bisects the infrared-reception-path 121 and the projection-path 123 evenly. Similarly, the angle between the incident-infrared-path 119 and the projection-path 123 is 2×φ, and the effective plane of the hot-mirror 107 bisects the incident-infrared-path 119 and the projection-path 123 evenly.

The LCOS panel 101d is positioned on a focal plane of the projection-lens 111 so that the image projected through the projection-lens 111 onto the object 113 is in focus. Also the infrared imaging-element 103 is positioned on a focal plane of the projection-lens 111 so that the image of the object 113 formed on the infrared imaging-element 103 is in focus. The LCOS panel 101d and the infrared imaging-element 103 may each be said to be conjugate to the hot-mirror 107 despite the deflected optical paths, meaning that the distance from the point of coincidence 107a to the LCOS panel 101d and the distance from the point of coincidence 107a to the infrared imaging-element 103 are the same for optical purposes, and that the angle φ in which the projection path 123 passes through on one side of the hot-mirror 107 is the same as the angle φ in which the infrared-reception-path 121 is reflected from the other side of the hot-mirror 107.

It is a particular advantage in the embodiment that the infrared-source 105 is placed to coincide with visible light from the LCOS only between the hot-mirror 107 and the object 113. The polarised-beam-splitter 109 would have absorbed much of the infrared if the infrared-source 105 was placed to share the same optical path with the light from the LCOS such that the infrared had to transmit through the polarised-beam-splitter 109. This would be due to polymeric coatings on the polarised-beam-splitter which are absorbent of infrared. Accordingly, infrared arriving at the object 113 would have been weakened and the infrared image captured by the infrared imaging-element 103 would not be sufficiently intense. The present arrangement improves the intensity of infrared reaching the object 113 by at least 50%. In contrast, the light from the visible light source 101a is very strong by intent in order to project an image and is weakened by the polarised-beam-splitter 109 significantly.

Accordingly, the infrared-source 105 is placed such that the incident-infrared-path 119 is coincident only from the point of coincidence 107a towards the object 113. This ensures that all these light paths are subject to the same distribution function of the projection-lens 111. This in turn ensures that the infrared image captured by the infrared imaging-element 103 and the visible image projected by the LCOS are fully coincident not only in terms of size, angle and orientation but also in spatial intensity of illuminance distribution; the infrared is not provided at an angle different to that of the projection-path 123. Having the same path to the object 113 allows the image projected from the LCOS panel 101d to have up to 85% uniformity in illuminance with the captured infrared imaged. The extent of the cast of shadows and the contrast one sees on the object 113 are thus faithfully reproduced in the projected image.

A further advantage is that the physical size of this embodiment can be made smaller compared to augmented reality projectors in which the incident-infrared-path 119 and the visible light augmented reality projector path are entirely not coincident. This leads to reduced material and manufacturing cost.

The infrared imaging-element 103 is typically a two-dimensional array of infrared detectors just like the LCOS panel 101d is a two-dimensional array of crystals. It is preferable that the area and aspect ratio of the array of liquid crystals on the LCOS panel 101d and the area and aspect ratio of the array of infrared detectors of the infrared imaging-element 103 are identical so that the image captured on the infrared imaging-element 103 and the image formed on the LCOS panel 101d are matching in size and aspect ratio. This further ensures matching field-of-view 125 between the projected image and the object 113.

Accordingly, the embodiment shows how, if the infrared-reception-path 121 and the projection-path 123 are coincident between the point of coincidence 107a and the object 113, and if the LCOS panel 101d and the infrared imaging-element 103 are conjugate to the hot-mirror 107, meaning that they are each at a focal plane of the projection-lens 111, and if the size of the image captured on the infrared imaging-element 103 and the size of the image formed on the LCOS panel 101d are identical, a highly matching field-of-view between the projected image and the object 113 can be achieved simply based on the described optical arrangements, without need of digital image processing.

In practice, however, LCOS panels and infrared detectors tend to be made by different third party manufacturers and it is difficult to purchase them with identical surface areas. It is more likely that the infrared imaging-element 103 is obtainable in a larger surface area than LCOS panels 101d. Many LCOS panels 101d are less than one inch square in area while infrared imaging-elements 103 may be slightly bigger. To overcome mismatch in area between the LCOS panel 101d and the infrared imaging-element 103, the field aperture 127 is placed in the focal plane of the projection-lens 111 instead of the infrared imaging-element 103. Thus, the infrared image is focused on the field aperture 127. The field aperture 127 can be adjusted in size to crop the infrared image into the same area as that of the crystal array on the LCOS panel 101d. In other words, the field aperture has a shape and size which are identical to the shape and size of the LCOS panel 101d. In this way, the image cropped by the field aperture 127 becomes identical with the image formed on the LCOS panel 101d except for image enhancements.

The infrared image is projected onto the half-mirror 109 from the field aperture 127 and deflected to the infrared imaging-element 103. An imaging lens (not shown) is used to focus the image on the infrared imaging-element 103 since the infrared imaging-element 103 is not located at the focal point of the projection-lens 111. The actual size and area of the infrared imaging-element 103 is not important any more as the image has already been cropped into one having the same area and size as the LCOS panel 101d. The image finally focused onto the infrared imaging-element 103 will maintain the aspect ratio as cropped by the field aperture 127 even if the infrared imaging-element 103 has a larger or smaller surface area than the LCOS panel 101d, and can be reproduced as an image on the LCOS panel 101d with exactly the same aspect ratio to be projected back onto the object 113 in matching field-of-view.

As the field aperture 127 effectively crops the image for the infrared imaging-element 103, the field aperture 127 shall be considered herein a part of and an extension of the infrared imaging-element 103.

Typically, the infrared image captured by the imaging-element 103 is processed digitally for image enhancement before being sent to the LCOS system 101 for projection. Signal-processing techniques such as edge detection, image sharpening, image averaging, contrast enhancement, colour-coding temperature regions and so on may be applied. This type of digital image processing is relatively straightforward and requires little processing power, unlike the digital image processing for fitting the image onto the object 113 for matching field-of-view.

Preferably, the projection-lens 111 is selected to provide a relatively long back focal length to provide sufficient space to accommodate the hot-mirror 107. In this embodiment, the back focal length is preferably at least 2 times the longest side or diameter of the polarize beam splitter.

Figure 3:
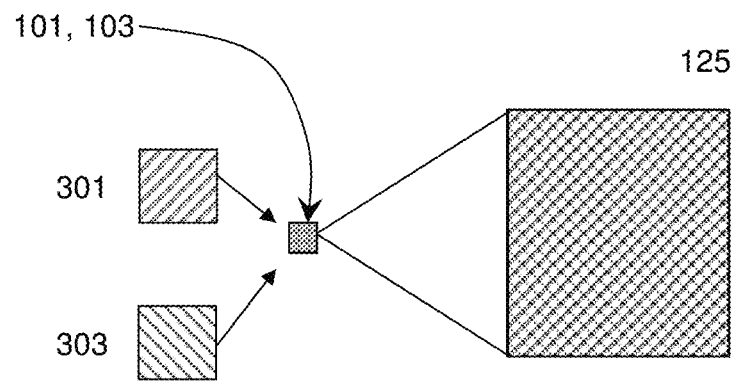
FIG. 3 illustrates the effects of the embodiment of FIG. 1.
Figure 4:
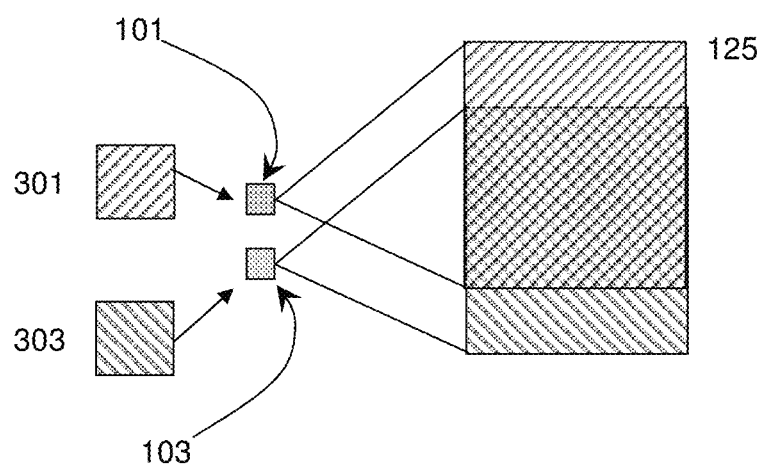
FIG. 4 illustrates the comparative effects of prior art.

FIG. 3 illustrates what is meant by matching the field-of-view 125 between the projected image and the object 113. Theoretically, if a camera 103 and a projector 101 have identical optical paths to an object 113, a processed image 301 projected from the projector 101 based on an original image 303 of the object 113 captured by the camera 103 can be precisely superimposed onto the object 113 in a matching field-of-view 125. The camera corresponds to the imaging-element 103 in this illustration. FIG. 4 is a comparative illustration showing how using a projector 101 and a camera 103 with separate optical paths results in misalignment between the projected image on the object 113, giving a poor match of field-of-view 125.

Figure 5:
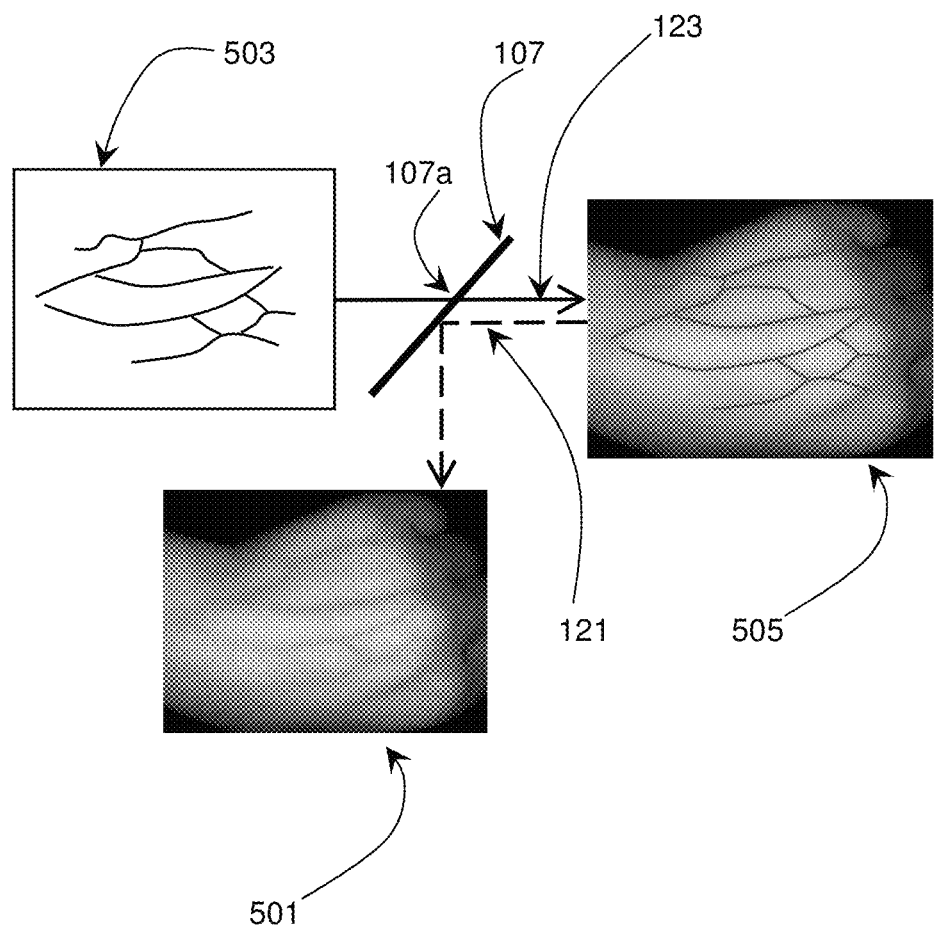
FIG. 5 series of image frames showing a process in the embodiment of FIG. 1.

FIG. 5 shows the images at the different parts of the image projector 100. The bottom picture 501 is an infrared image of a hand captured by the infrared imaging-element 103. The image is processed into visible colours 503, showing the locations of blood vessels in the hand and sent to the LCOS 101 for projection. When projected onto the hand, the surface of the hand is now augmented visually 505 indicating the exactly location of the blood vessels in the hand. If the optical path of capturing the infrared image is coincident with the optical path of the projected image, and if the size of the projected image is exactly the same as the hand, the projected image and the hand will be perfectly aligned in a matching field-of-view 125 and blood vessels in the human hand can be precisely indicated by the projected image.

Figure 6:
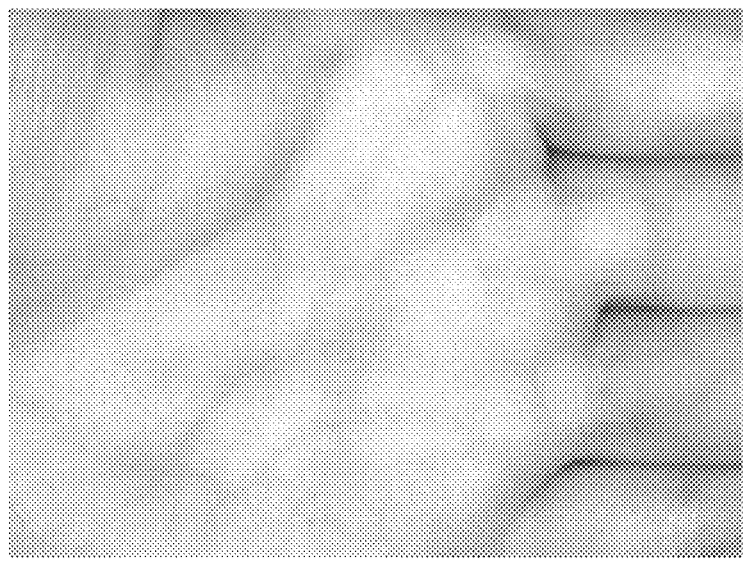
FIG. 6 is a photograph showing the effects of the embodiment of FIG. 1.

FIG. 6 is an infrared image showing how small blood vessels in a human palm can be accentuated and indicated clearly in near-infrared. This infrared image can be processed into visible colours and be projected back onto the palm in visible light.

Figure 7:
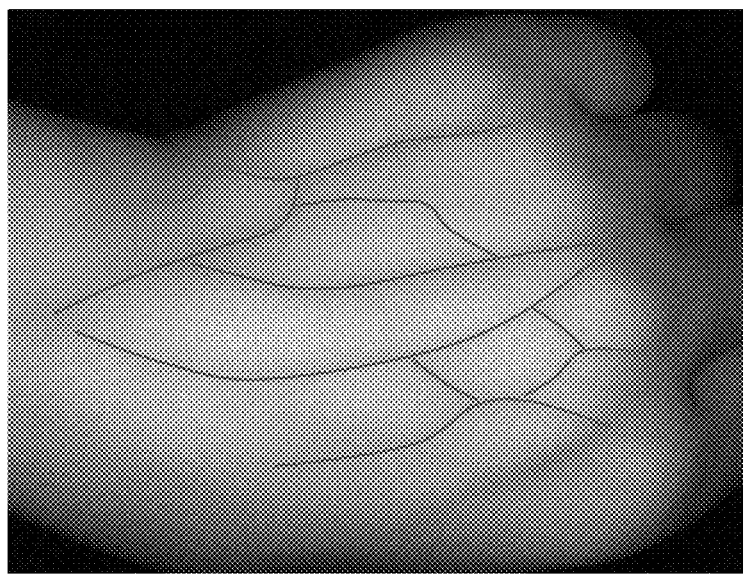
FIG. 7 is a photograph showing the effects of the embodiment of FIG. 1.

FIG. 7 is another image showing how blood vessels in the back of a hand can be indicated clearly by projecting the hand's infrared image back onto the hand in visible light.

Figure 8:
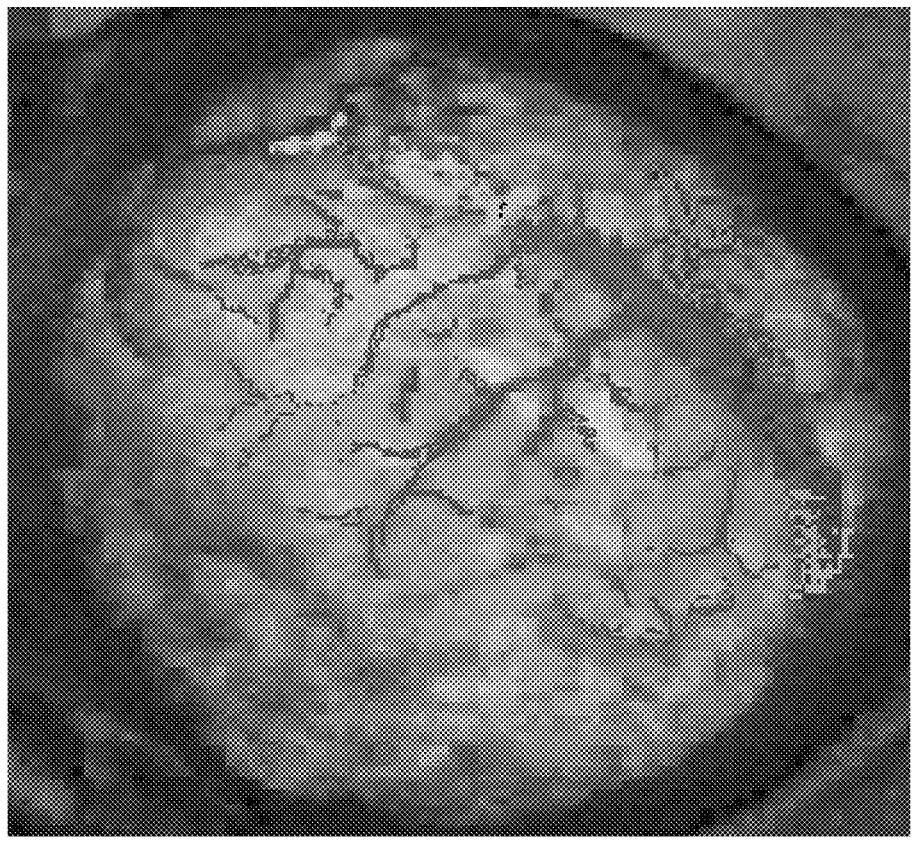
FIG. 8 is a photograph showing the effects of the embodiment of FIG. 1.

FIG. 8 is a fabricated picture of how the augmented reality projector 100 can be used in brain surgery to indicate the location of blood vessels in the brain.

Figure 9:
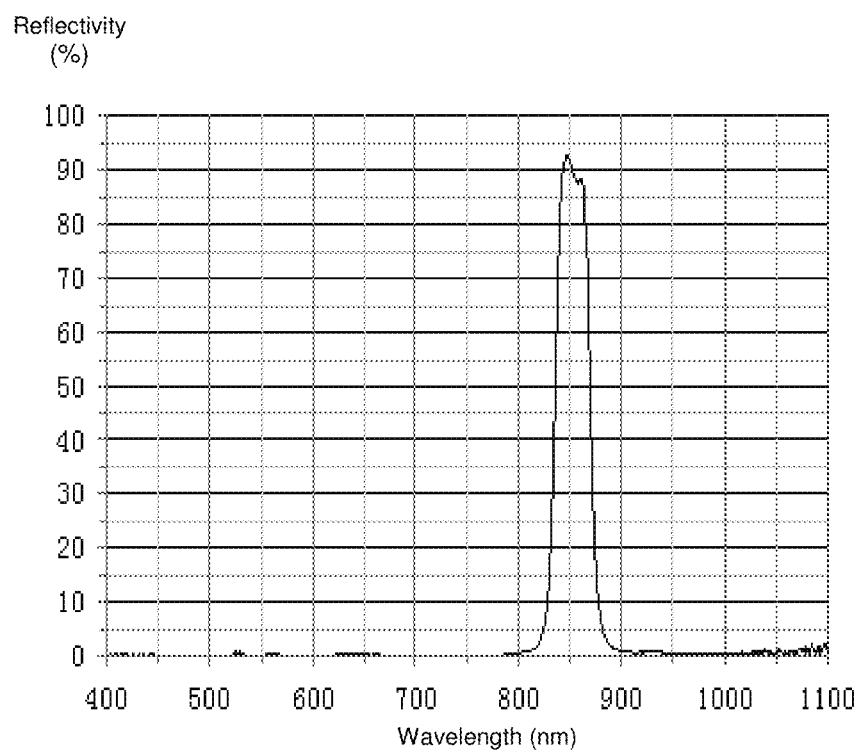
FIG. 9 is a chart illustrating a characteristic of a component in the embodiment of FIG. 1.

The wavelength ($\lambda$) of infrared is between 780 nm to 1100 nm. Therefore, the infrared-source 105 can be selected to emit in any wavelength within this range. It is preferable that the infrared is emitted in a single wavelength or within a narrow range of wavelengths in order for the captured infrared image to have good contrast. For example, the selected wavelength of 850 nm can have a range within ±25 nm, from 825 nm to 875 nm as illustrated in the chart shown as FIG. 9. Optionally, the hot-mirror 107 can be selected to filter or allow only a narrow range of infrared wavelengths to pass through instead of controlling the wavelength range emit-able by the infrared-source 105. This relieves any need for an infrared filter to be placed before the infrared image sensor to removed interfering light, providing the possibility of a yet more compact augmented reality projector 100. Thus, the hot-mirror 107 helps to prevent visible light from the LCOS system 101 from straying into the infrared imaging-element 103, which increases the clarity and contrast in the infrared image captured by at least 50% compared with situations where visible light may interfere with the infrared imaging-element 103.

Figure 10:
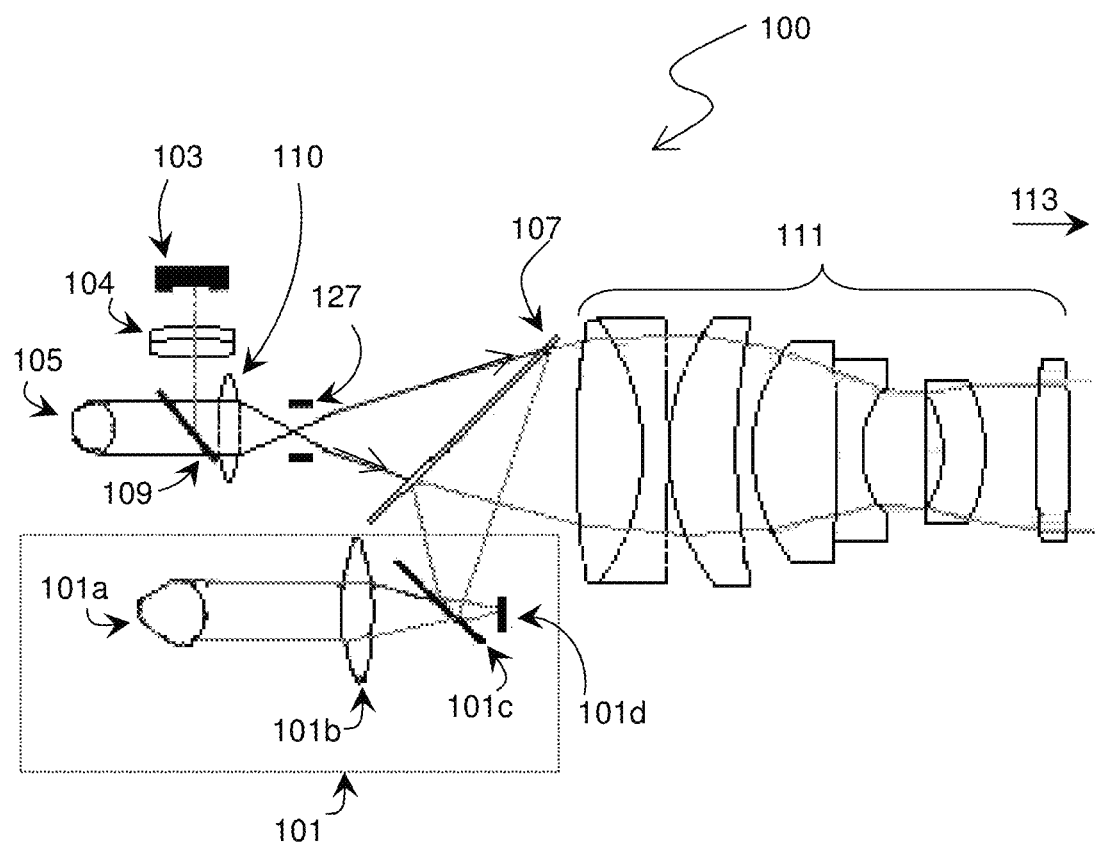
FIG. 10 is a schematic illustration of another embodiment.

FIG. 10 illustrates a further embodiment to that of FIG. 2. In this embodiment, a cold mirror 107 is used instead of a hot-mirror 107. The cold mirror 107 has surface coating which reflects narrower, visible wavelengths such as instead of broader wavelengths like infrared. Therefore, the infrared-source 105 is arranged such that the infrared passes through the cold mirror 107 without deflection, and is in line with the projection-path 123 to the object 113. However, the LCOS panel 101d is arranged to project visible light onto the cold mirror 107 only to be deflected by the cold mirror 107 towards the object 113. In this embodiment, the infrared-reception-path 121 and the projection-path 123 are still coincident between the point of coincidence 107a and the object 113. The field aperture 127 for cropping the infrared image is still provided at the focal plane of the projection-lens 111 along the infrared-reception-path 121 which crops the infrared image into the same size and area as the liquid crystal array of the LCOS panel 101d. An imaging lens 104 is there used to focus the cropped image onto the surface of the infrared imaging-element 103. The projection-lens 111 is now a series of lens 111 for focusing onto the object 113 in a far distance.

Figure 11:
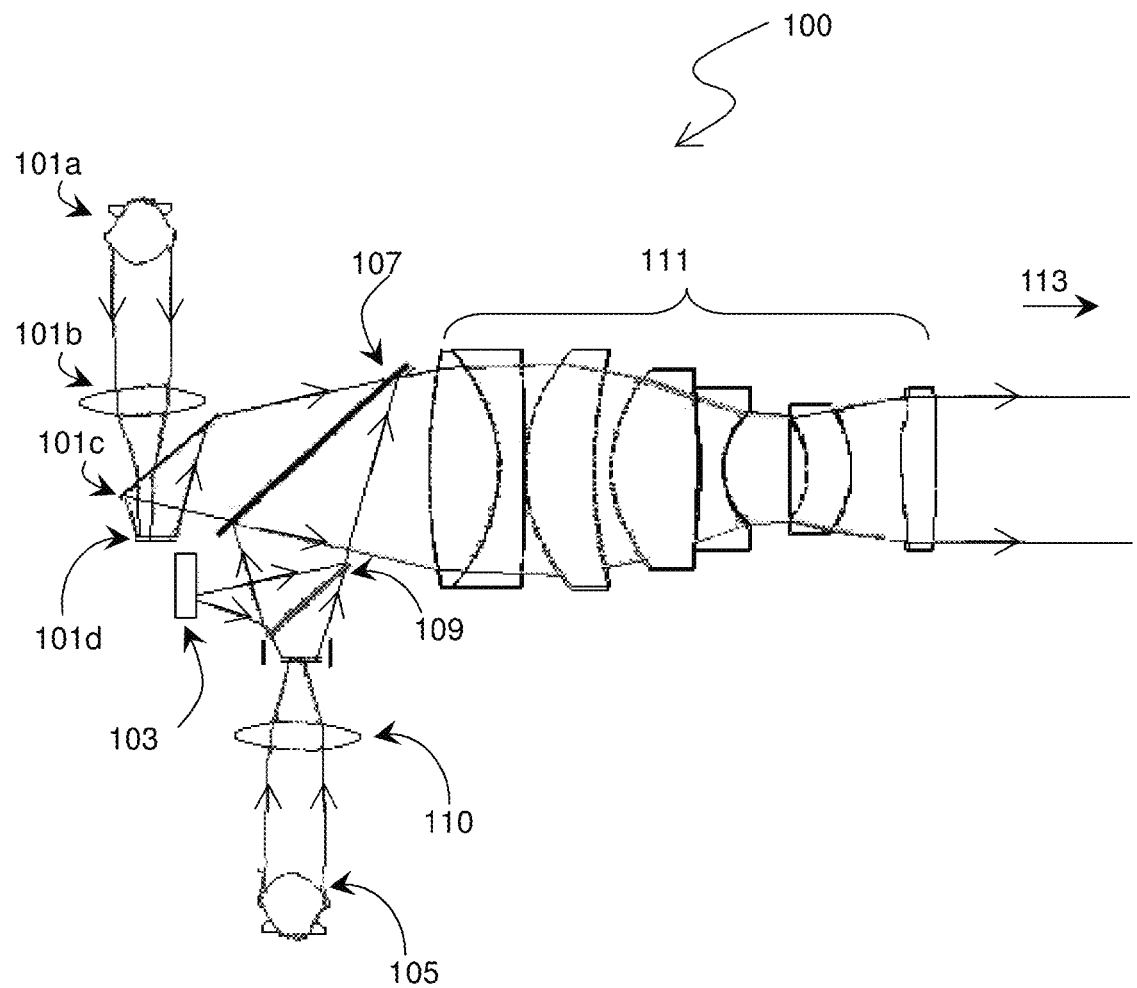
FIG. 11 is a schematic illustration of another embodiment.

FIG. 11 is yet another embodiment 100 to that of FIG. 2, in which a hot-mirror 107 is used again to divert infrared while allowing visible light to pass straight through. The infrared imaging-element 103 itself is placed in the focal plane of the projection-lens 111. The array of infrared detectors in the infrared imaging-element 103 has the same surface area as the crystal array in the LCOS panel 101d and, therefore, there is no need of a field aperture 127 to adjust the size of the infrared image.

Figure 12:
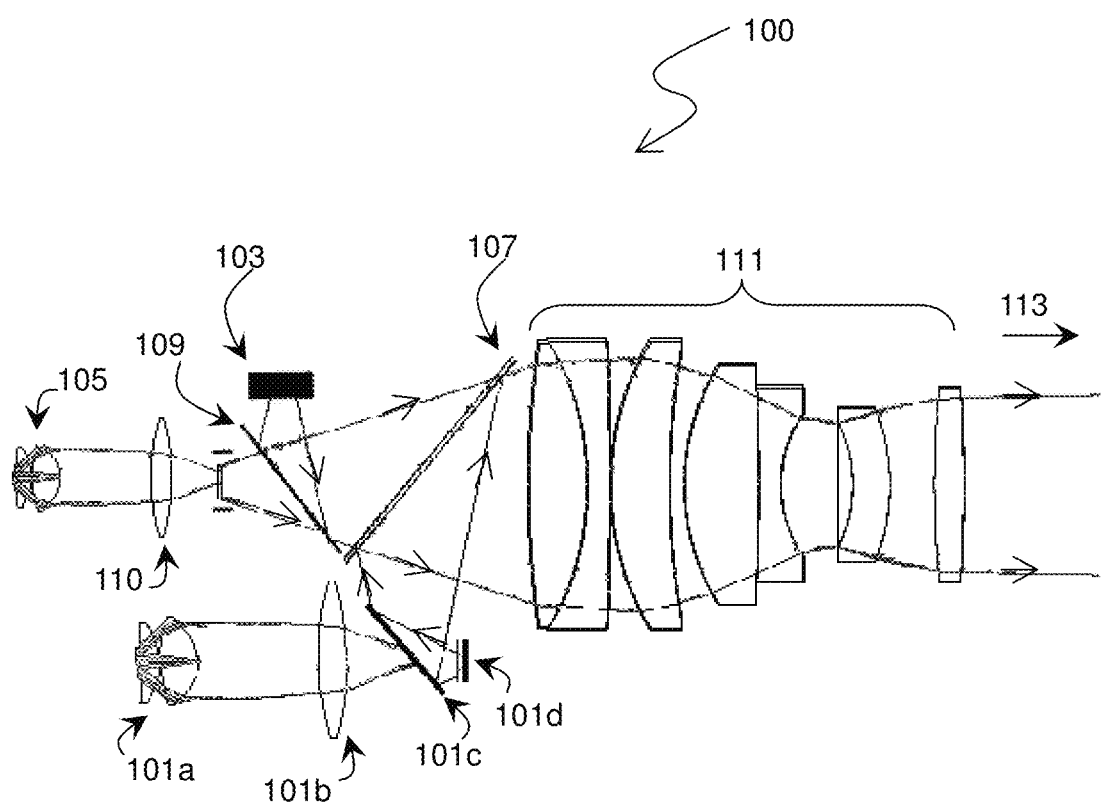
FIG. 12 is a schematic illustration of another embodiment.

FIG. 12 shows yet another embodiment which uses a cold mirror 107. The infrared imaging-element 103 is placed in the focal plane of the projection-lens 111 so that the captured image is focused on the infrared imaging-element 103. The array of infrared detectors in the infrared imaging-element 103 has the same surface area as the crystal array in the LCOS panel 101d and there is no need for any field aperture 127 to crop the image formed on the infrared imaging-element 103.

Figure 13:
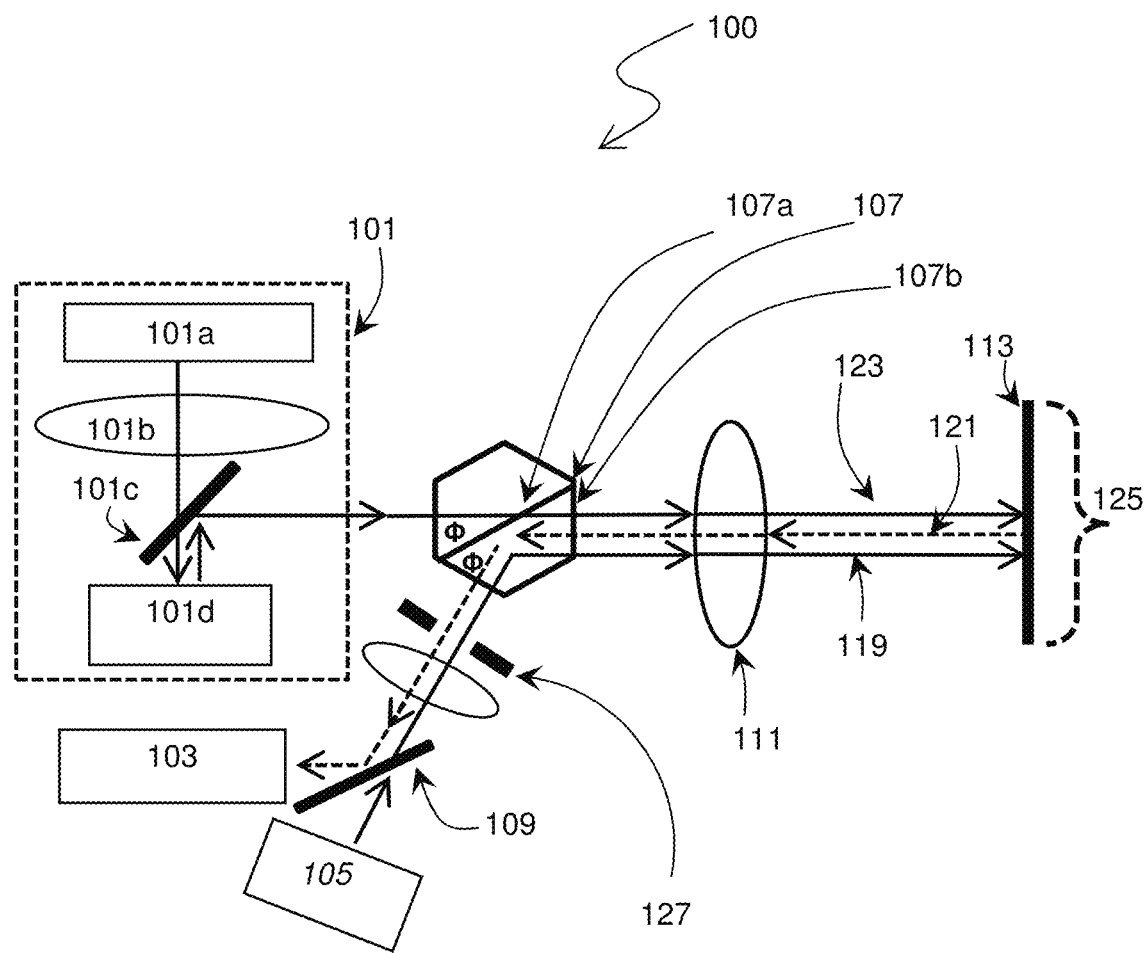
FIG. 13 is a schematic illustration of another embodiment.

FIG. 13 shows yet another embodiment which is a variation of the embodiment of FIG. 2. The hot mirror is replaced with a symmetrical polyhedron prism 107b having a layer of coating across the centre of the prism and functioning as the wavelength-selective interference-splitter 107. In this embodiment, the entire polyhedron prism 107b functions in the same way as the hot-mirror 107. The infrared light in both the incident-path 119 and the reception-path 121 are reflected by the polyhedron prism 107b while the projection-path 123 passes through the polyhedron prism 107b to the object 113. Using the polyhedron prism 107b allows the additional advantage of orienting all the optical incident-path 119, the reception-path 121 and the projection-path to enter or leave the polyhedron prism 107b in any one of the surfaces of the polyhedron prism 107b at right angle, which prevents unwanted refraction moving the position of the incident-path 119, the reception-path 121 and the projection-path. The choice of the interference-splitter 107 may also be selected also to work with the density of the prism material to reduce refraction. It is a known fact that reduction of refraction when light passes through a medium can reduce unwanted aberrations and this needs no elaboration here. Therefore, this embodiment can produce even sharper field-of-view match to due reduced aberration. The field aperture 127 is also used in this case. Therefore, the LCOS panel 101d and the field aperture 127 are conjugate to the polyhedron prism 107b, meaning that the distance from the point of coincidence 107a inside the polyhedron prism 107b to the LCOS panel 101d and the distance from the point of coincidence 107a to the field aperture 127 are the same for optical purposes, and that the angle φ in which the projection path 123 passes from one side of the interference-splitter 107 in the polyhedron prism 107b is the same as the angle φ in which the infrared-reception-path 121 is reflected from the other side of the interference-splitter 107. The polyhedron prism 107b in the drawing is a six sided hexahedron prism and φ has the general range of 0°<φ<45°. However, but other kinds of polyhedron may be used provided the angle φ is accurately adjusted for each case. In alternative embodiments, the interference-splitter 107 can be selected to reflect 'cooler' wavelengths and allowing 'warmer' wavelengths to pass through as in a cold mirror, so that the visible light is reflected instead of the infrared, as described for the embodiment of FIG. 10.

Figure 14:
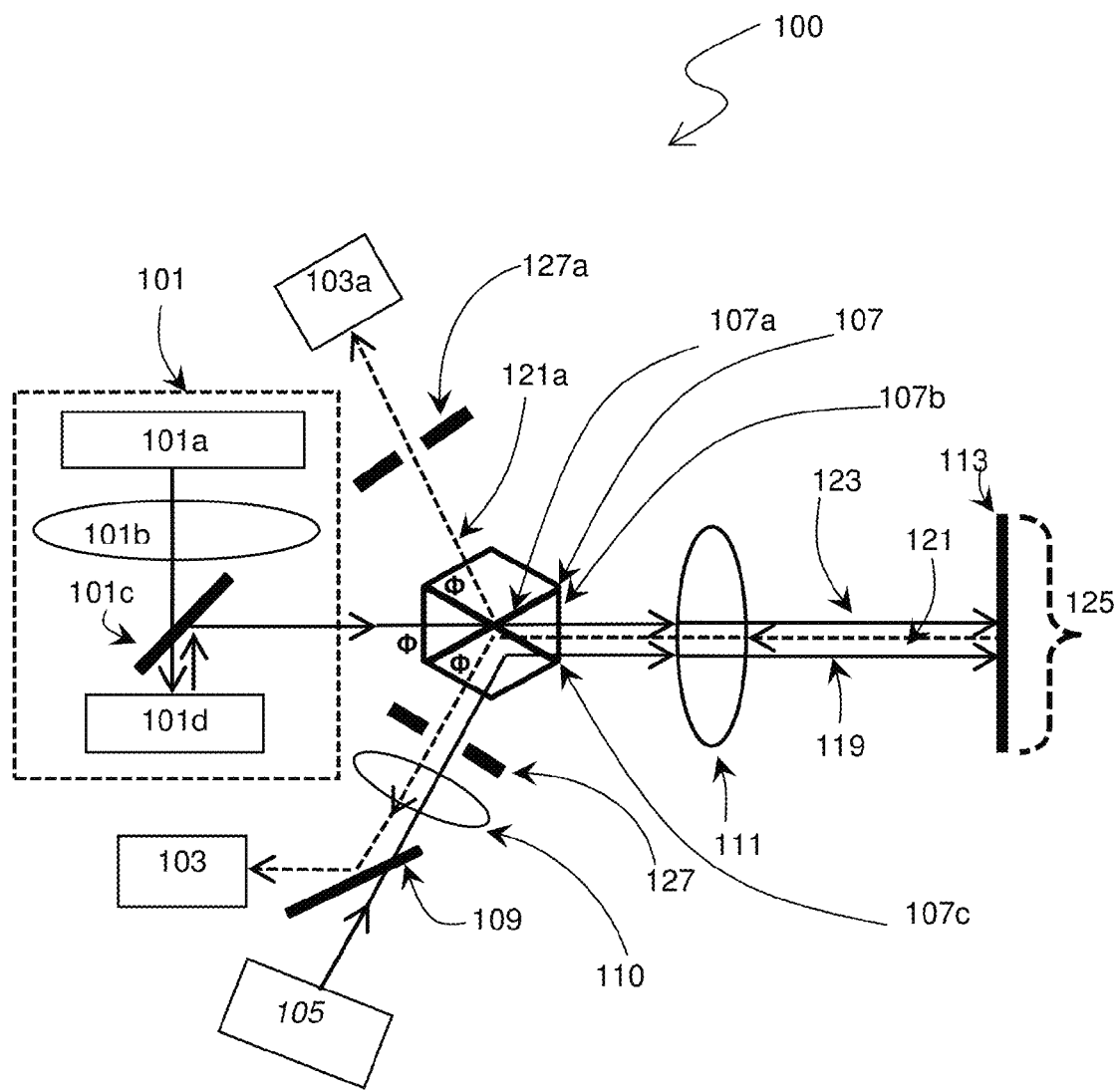
FIG. 14 is a schematic illustration of another embodiment.

FIG. 14 shows yet a further embodiment which is a variation to that of FIG. 13. The symmetrical polyhedron prism 107b in this case has two layers of interference-splitters 107, 107c, behaving as two hot mirrors. The second interference-splitter 107c is positioned to cross the first interference-splitter 107 at the point of coincidence 107a, so that the infrared-reception-path 121 can be split into two 121, 121a, and so that two different infrared imaging-elements 103, 103a can be used to capture two infrared images. In other words, use of a polyhedron with two interference-splitters 107, 107c inside provides be possibility of allowing a second imaging-element 103a to be integrated into the image projector 100. In order for the fields-of-view of both captured images to be matching, the reflection angle φ between the second reception path 121a and the effective plane of the second interference-splitter 107c is also φ, which is the same angle φ between the infrared-reception-path 121 and the effective plane of the first interference-splitter 107, which is also the same angle φ between the projection-path 123 and the effective plane of the first interference-splitter 107. As a hexahedron prism is used in this embodiment, the angle φ being within the range of 0°<φ<45°. As with the embodiment of FIG. 2, a field aperture 127 is used to crop and adjust the area and size the image of the object 113 at the focal plane of the projection-lens 111 before the image is captured by the imaging-element 103. A second field aperture 127a is provided crop and adjust the area and size of the image captured on the second imaging element 103a. The drawing does not show an illumination lens and a half-mirror adjacent this second field aperture 127a because there is no light-source 105 located near the second imaging element 103a. Accordingly, both images captured by the two imaging elements 103, 103a can be combined at the LCOS panel 101d and projected onto the object 113 in a matching field-of-view.

In a variation of this embodiment, the second interference splitter 107c may be a cold mirror instead of a hot mirror, which reflects ultraviolet. Therefore, the second imaging-element 103a can be used to capture images in other ultra-violet. This allows images in several ranges of invisible wavelengths to be captured, converted into visible colours and superimposed onto the object 113 in a matching field-of-view. This embodiment is useful in the case where the object 113 has different information which may be revealed under different wavelengths of light and when it is desirable to superimpose such different information in visible light onto the object 113 at the same time. In another variation of this embodiment, the second interference splitter 107c may be a hot mirror but which has a different frequency range to that of the first interference splitter. Therefore, different information which can be obtained in different ranges of infrared wavelengths may be obtained separately and then re-combined in the projected image. In yet another variation of this embodiment, the second interference splitter 107c is not a wavelength-based interference splitter but is a half-mirror. This allows the second to capture images in visible light while the first imaging-element 103 capture images in infrared.

Using two imaging-elements 103, 103a may allow colour-based three-dimensional effects to be generated in the LCOS, as the skilled man would know and which needs no elaboration here.

Under a different inventive aspect, the two interference-splitters 107, 107c may be replaced by two half-mirrors. In this case, the two half-mirrors 107, 107c split light without being wavelength selective and the two imaging-elements 103 can be selected to capture images in any wavelength including visible and invisible wavelengths.

Figure 15:
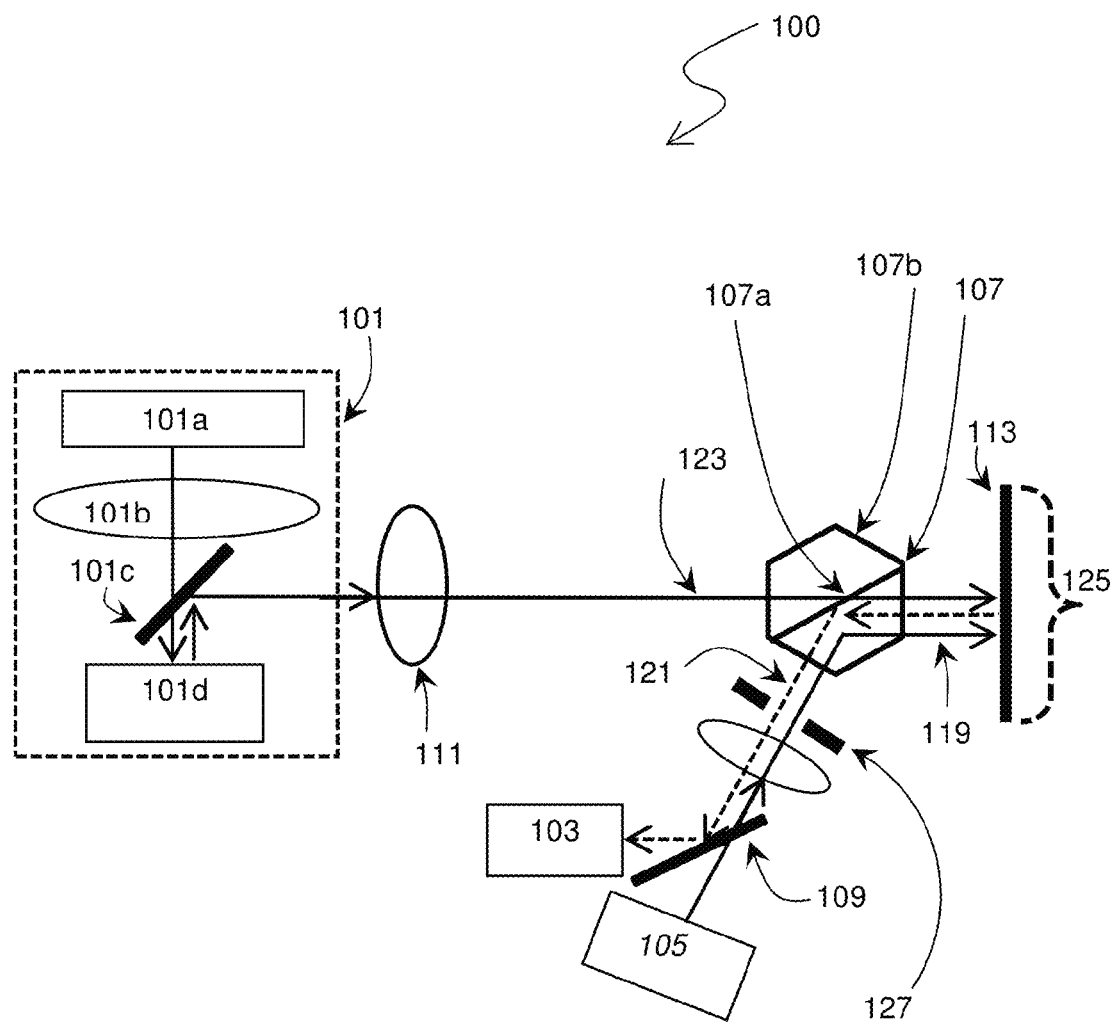
FIG. 15 is a schematic illustration of another embodiment.

FIG. 15 shows a variation to the embodiment of FIG. 13, the different being that the polyhedron prism 107b is placed between the projection-lens 111 and the object 113. In this case, the image on the infrared imaging-element 103 is not in the focal plane of the projection-lens 111 and may have to be focused by another set of lens (not shown). Although the projected image and the captured infrared image do not experience the same luminance distribution or transfer function of the projection-lens 111 in this case, the field aperture 127 can nevertheless still be used to adjust the area and size of the infrared image captured on the infrared imaging element 103, so as to match the area and size of the image formed on the LCOS panel 101d, which provides the possibility of matching the field-of-view of the projected image and the object 113.

Figure 16:
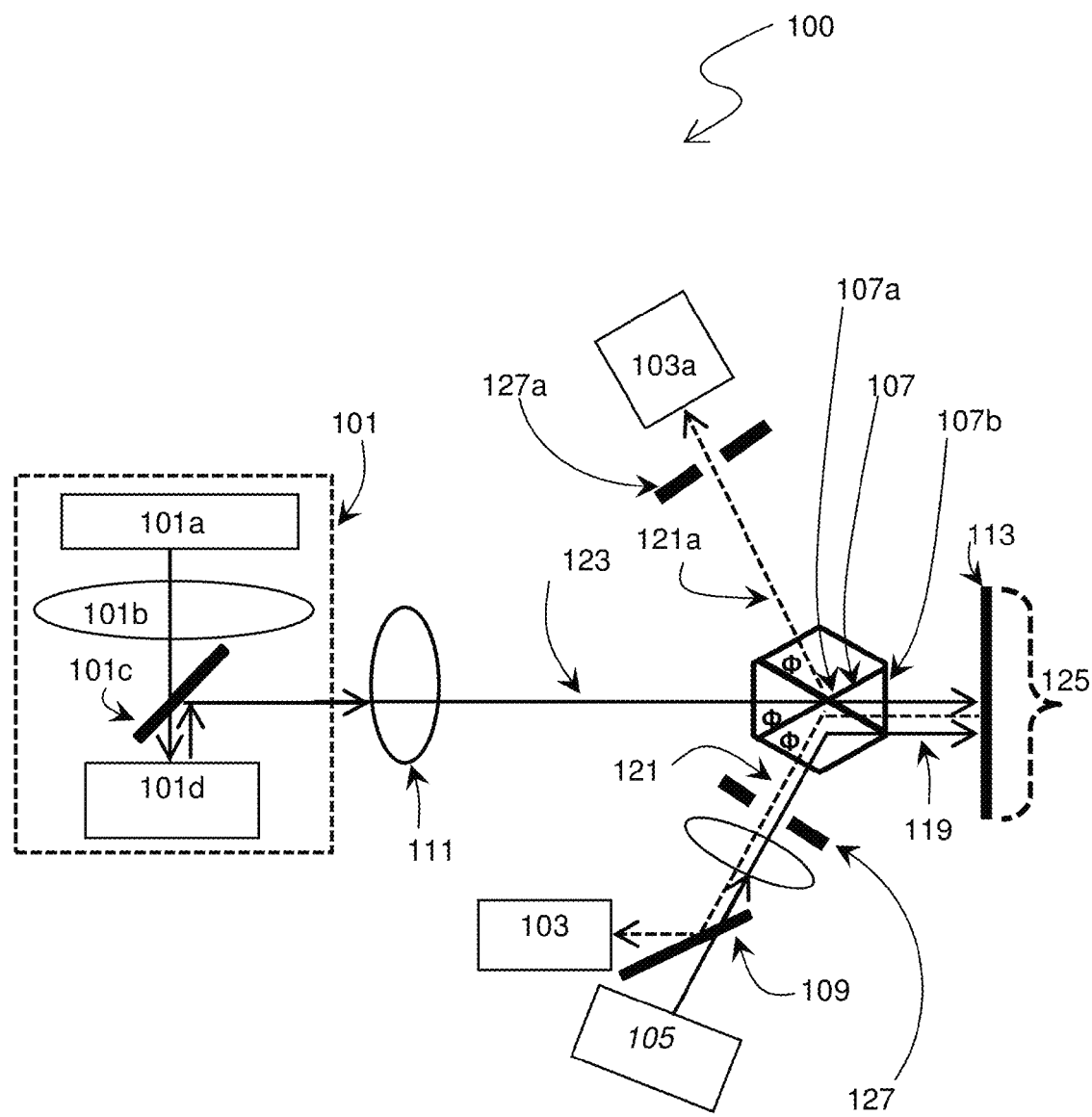
FIG. 16 is a schematic illustration of another embodiment.

FIG. 16 shows a variation to the embodiment of FIG. 14, the different being that the polyhedron prism 107b is placed between the projection-lens 111 and the object 113. As with FIG. 14, there are two imaging elements 103, 103a. In this case, the focus of the image on the infrared imaging-element 103 and the second imaging-element 103a is not in the focal plane of the projection-lens 111 and may have to be focused by another set of lens (not shown). The field aperture 127 for the infrared imaging element 103 and the additional field aperture 127a for the additional imaging element 103a can be used to adjust the field-of-view of the infrared images captured on both the infrared imaging elements 103, 103a so as to match the field-of-view of the image formed on the LCOS panel 101d to the object's 113.

Figure 17:
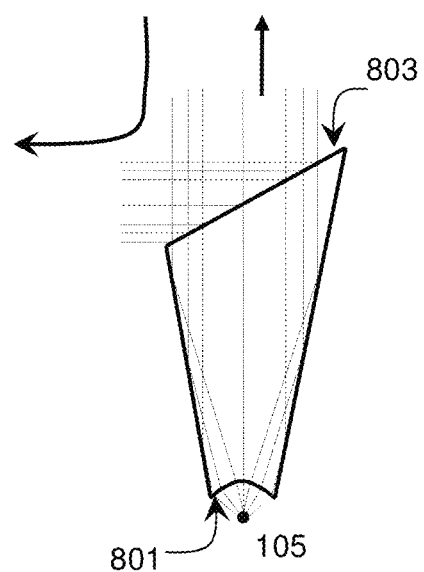
FIG. 17 shows a lens useable in the embodiments.

FIG. 17 shows a lens which can be used instead of the half-mirror 109 at the infrared-source 105. The lens has a collimating surface 801 through which infrared from the infrared-source 105 passes and is distributed by the internal reflecting surface of the lens, which achieves the same luminance distribution effect of an illuminating lens. The infrared exits through a splitting surface without deflecting from the forward light path. In the reverse direction, however, infrared from the hot-mirror 107 or cold mirror 107 arriving at the splitting surface is deflected at an angle towards the infrared image sensor (not illustrated here). This lens is therefore a combination of an illuminating lens and a half-mirror in function, and can be used in any of the described embodiments.

Figure 18:
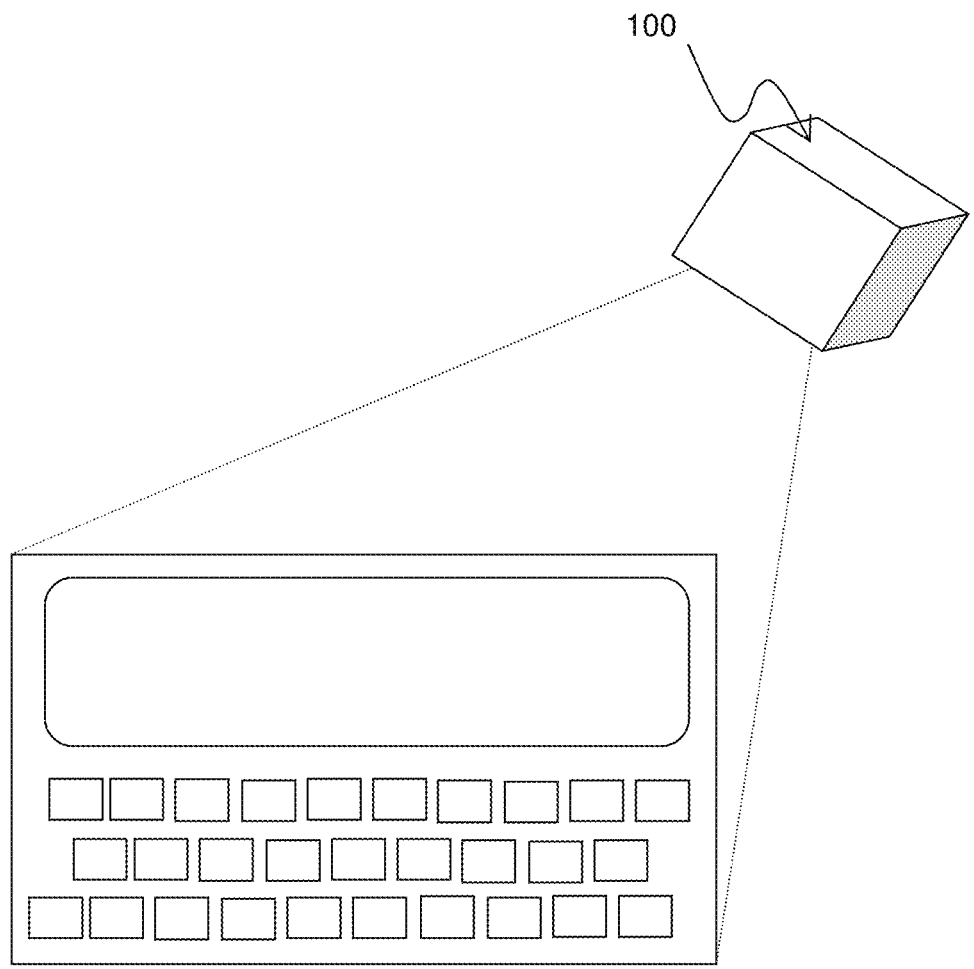
FIG. 18 shows another embodiment and an application thereof.

The described embodiments therefore use an optical system to ensure that the projected image has a good match to the field-of-view with the object 113. Although the image may be digital processed for visual enhancement before the projector-element 101 projects the processed image onto the object 113, the resource requirement for such enhancements is remarkably less than that required to adjust and achieve field-of-view matching. This provides the possibility that processing power is freed up to allow real time image refresh, and allows the appearance of a moving object 113 to be continuously augmented. This provides that, other than using the described embodiments for augmenting the appearance of human parts in medical procedures, more mundane lifestyle applications are also possible. For example, FIG. 18 shows a virtual typing keyboard projected from an augmented reality projector 100 onto a flat surface. As the embodiments provided the possibility of reduced reliance on software processing and instead relying on optical arrangements to ensure good field-of-view match, a human hand moving and tapping on the virtual keyboard can be detected and monitored in real time by infrared. By providing the possibility of excellent field-of-view matching between the physical hand and the infrared image of the hand, the position of the finger on the virtual keyboard can be accurately deduced. This precise detection of the user's finger allows the projected keyboard to have accurate responsiveness to interaction with the hand. This application relieves the need for a keyboard for a computer. It is particularly useful in a place where a keyboard input is desirable but the situation is such that it is inconvenient to provide an actual keyboard. For example, a keyboard can be projected on the food tray in a passenger seat in a plane for interacting with an entertainment screen. Preferably, since the embodiments provide that the human hand can be detected in real time, the part of the virtual keyboard which would have been projected onto the back of the user's hand is blacked-out so that no images are formed on the back of the hand (not illustrated). In other words, a negative image of the hand can be formed in the projected keyboard matching the hand. The quick image refreshing made possible by the embodiments can continuously black out a portion of the keyboard which matches the user's moving hand. This could give a 'real' feel in the projected keyboard, because the user may not notice that the keyboard is actually a projected image.

In another application of the embodiment, a virtually generated menu is provided by the image projector 100 which is projected on a table in a restaurant. The projected menu is user interactive and the customer of the restaurant can pick through the menu with his fingers. This relieves the need for printing menus and allows the customer to order food by picking on the user interactive menu. Again, the part of the menu which would have been projected onto the user's hand can be blacked out so that no images are formed on the back of the user's hand.

Therefore, the embodiments provide a possibility of interactive graphical user interface (GUI) without need of a screen or computer tablet.

In another application of the embodiments, a menu is projected by the image projector 100 onto the wall of a fashion retail outlet where the customer can select the clothes by picking on a virtual menu projected into a wall.

Where 'a wavelength' has been used herein, the skilled reader understands this may include 'at least one wavelength', and that in some embodiments a monochromatic wavelength may be part of a polychromatic range of wavelengths for achieving any same purpose. For example, if the mentioned visible light comprises white light, then the 'wavelength' of the white light is typically made up of the wavelengths in red, green and blue ranges.

Accordingly, the embodiments described is an image projector 100 comprising: an imaging-element 103 for capturing an image of an object 113 in a reception-path 121 in at least one first wavelength; a projection-element 101 for projecting an image onto the object 113 in an projection-path 123 in at least one second wavelength; a wavelength selective interference-splitter 107 for reflecting either one of the at least one first wavelength and the at least one second wavelength, and allowing passage of the other one of the at least one first wavelength and the at least one second wavelength; the imaging-element 103 and the projection-element 110 arranged such that either one of the projection-path 123 and the reception-path 121 passes through the interference-splitter 107, while the other one of the projection-path 123 and the reception-path 121 is reflected by the interference-splitter 107; the interference-splitter 107 coinciding the projection-path 123 and the reception-path 121 between the interference-splitter 107 to the object 113; the interference-splitter 107 separating the projection-path 123 and the reception-path 121 from the interference-splitter 107 to the respective projection-element 101 and imaging-element 103; wherein the projection-path 123 between the projection-element 101 to the interference-splitter 107 is conjugate with the reception-path 121 between the interference-splitter 107 and the imaging-element 103.

Typically, the imaging-element 103 has a sensor surface; the projection-element 101 has a projection surface 101d; and the area of the sensor surface and area of the projection surface 101d are substantially the same. Alternatively, the projection-element has a projection surface 101d, the imaging-element including a field aperture 127, the field aperture 127 being the part of the imaging-element 103 conjugate to the interference-splitter 107; and the field aperture 127 is suitable for cropping an image received on the field aperture 127 to have substantially the same size and area as the projection surface 101d.

Also, an image projector 100 is described comprising: a first light-source 105 for projecting light onto an object 113 in an incident-path 119 in at least one first wavelength; a projection-element 101 for projecting an image onto the object 113 in an projection-path 123 in at least one second wavelength; a wavelength selective interference-splitter 107 for reflecting either one of the at least one first wavelength and the at least one second wavelength, and allowing passage of the other one of the at least one first wavelength and the at least one second wavelength; the light-source 105 and the projection-element 101 arranged such that either one of the projection-path 123 and the incident-path 119 passes through the interference-splitter 107, while the other one of the projection-path 123 and the incident-path 119 is reflected by the interference-splitter 107; the interference-splitter 107 coinciding the projection-path 123 and the incident-path 119 between the interference-splitter 107 to the object 113; the interference-splitter 107 separating the projection-path 123 and the incident-path 119 from the interference-splitter 107 to the respective projection-element 101 and light-source 105.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

Although infrared has been described as the invisible light, it is possible that light of other wavelengths may be used instead. For example, ultraviolet radiation may be used instead of infrared when examining objects such as plants or ultraviolet sensitive animal tissues. Furthermore, the imaging-element may capture images in fluorescent or phosphorescent emission. Furthermore, it is also possible that two monochromatic visible light wavelengths may be used instead of the described pairing of visible and invisible wavelengths, the choice depending on whether capturing images in one wavelength can reveal or accentuate information which is not available in the other wavelength.

The skilled man understands that while LCOS has been described as part of the embodiments, similar technology for projecting an image using reflective technology may be used, such as Digital Light Processing technology.

Although the drawings illustrate the incident-infrared-path 119, the infrared-reception-path 121 and the projection-path 123 two-dimensionally, and describe the angle φ two-dimensionally, the skilled reader will understand that coinciding the incident-infrared-path 119, the infrared-reception-path 121 and the projection-path 123 is to be understood in three dimension.

What is claimed is:

1. An image projector comprising:
   an imaging-element that has a field aperture and that captures an image of an object in a reception-path in at least one first wavelength;
   a projection-element that has a projection surface and that projects the image onto the object in a projection-path in at least one second wavelength;
   an interference-splitter for reflecting either one of the at least one first wavelength and the at least one second wavelength, and allowing passage of the other one of the at least one first wavelength and the at least one second wavelength;
   the imaging-element and the projection-element arranged such that either one of the projection-path and the reception-path passes through the interference-splitter, while the other one of the projection-path and the reception-path is reflected by the interference-splitter;
   the interference-splitter coinciding the projection-path and the reception-path between the interference-splitter to the object;
   the interference-splitter separating the projection-path and the reception-path from the interference-splitter to the respective projection-element and imaging-element;
   wherein the projection-path between the projection-element to the interference-splitter is conjugate with the reception-path between the interference-splitter and the imaging-element;
   wherein the field aperture is a part of the imaging-element conjugate to the interference-splitter; and
   wherein the field aperture crops the image received on the field aperture to have substantially the same area as the projection surface.

2. The image projector as claimed in claim 1, wherein:
   the imaging-element has a sensor surface; and
   the area of the sensor surface and the area of the projection surface are substantially the same.

3. The image projector as claimed in claim 1, wherein:
   the image projected by the projection-element is the image of the object captured by the imaging-element.

4. The image projector as claimed in claim 1, wherein: the image is an enhanced image.

5. The image projector as claimed in claim 1, wherein:
   the image projected by the projection-element has a blacked-out portion; and
   the back-out portion has a matching field-of-view with the object.

6. The image projector as claimed in claim 1, wherein:
   the second wavelength is within a visible light range of wavelengths.

7. The image projector as claimed in claim 1, wherein:
the first wavelength is invisible to human eyes.

8. The image projector as claimed in claim 7, wherein:
the first wavelength is infrared.

9. The image projector as claimed in claim 7, wherein:
the first wavelength is ultra-violet.

10. The image projector as claimed in claim 1, wherein:
a projection-lens is placed between the interference-splitter and the object.

11. The image projector as claimed in claim 1, wherein:
the interference-splitter is encapsulated in a prism.

12. The image projector as claimed in claim 1, further comprising:
a second imaging-element; and
the prism capsulate a second interference-splitter; wherein
the second interference-splitter further separates the projection-path and a second reception-path to the respective projection-element and the second imaging-element; and
the projection-path between the projection-element to the interference-splitter is conjugate with the second reception-path between the interference-splitter and the second imaging-element.

13. The image projector as claimed in claim 1, further comprising:
a first light-source for projecting light onto an object in an incident-path in the at least one first wavelength;
the light-source and the projection-element arranged such that either one of the projection-path and the incident-path passes through the interference-splitter, while the other one of the projection-path and the incident-path is reflected by the interference-splitter;
the interference-splitter coinciding the projection-path and the incident-path between the interference-splitter to the object;
the interference-splitter separating the projection-path and the incident-path from the interference-splitter to the respective projection-element and light-source.

14. The image projector as claimed in claim 1, wherein the image is a graphical user interface.

15. The image projector as claimed in claim 1, wherein the image is an interactive keyboard.

16. An image projector comprising:
a first light-source for projecting light onto an object in an incident-path in at least one first wavelength;
a projection-element for projecting an image onto the object in an projection-path in at least one second wavelength and including a second light-source and a reflective projector-element;
an interference-splitter for reflecting either one of the at least one first wavelength and the at least one second wavelength, and allowing passage of the other one of the at least one first wavelength and the at least one second wavelength;
the light-source and the projection-element arranged such that either one of the projection-path and the incident-path passes through the interference-splitter, while the other one of the projection-path and the incident-path is reflected by the interference-splitter;
the interference-splitter coinciding the projection-path and the incident-path between the interference-splitter to the object;
the interference-splitter separating the projection-path and the incident-path from the interference-splitter to the respective projection-element and light-source;
wherein the second light-source for projecting light is in the at least one second wavelength onto the reflective projector-element, such that the reflective projector-element projects an image onto the object in the projection-path;
wherein the second light-source projects light onto the reflective projector-element though a polarised-beam-splitter.

17. An image projector comprising:
an imaging-element that has a sensor surface and that captures an image of an object in a reception-path in at least one first wavelength;
a projection-element that has a projection surface and that projects the image onto the object in a projection-path in at least one second wavelength;
an interference-splitter for reflecting either one of the at least one first wavelength and the at least one second wavelength, and allowing passage of the other one of the at least one first wavelength and the at least one second wavelength;
the imaging-element and the projection-element arranged such that either one of the projection-path and the reception-path passes through the interference-splitter, while the other one of the projection-path and the reception-path is reflected by the interference-splitter;
the interference-splitter coinciding the projection-path and the reception-path between the interference-splitter to the object;
the interference-splitter separating the projection-path and the reception-path from the interference-splitter to the respective projection-element and imaging-element;
wherein the projection-path between the projection-element to the interference-splitter is conjugate with the reception-path between the interference-splitter and the imaging-element;
wherein the area of the sensor surface and the area of the projection surface are substantially the same.

* * * * *